United States Patent [19]

Asato et al.

[11] 4,239,708

[45] Dec. 16, 1980

[54] P-PHENYLENE BIS[IMINO(THIOCARBONYL)] DIPHOSPHORAMIDIC ACID ESTERS AS ANTHELMENTIC AGENTS

[75] Inventors: Goro Asato, Titusville; John A. Pankavich, Trenton, both of N.J.

[73] Assignee: American Cyanamid Company, Stamford, Conn.

[21] Appl. No.: 16,678

[22] Filed: Mar. 1, 1979

Related U.S. Application Data

[63] Continuation-in-part of Ser. No. 903,293, May 5, 1978, abandoned, which is a continuation-in-part of Ser. No. 819,304, Jul. 27, 1977, abandoned, which is a continuation-in-part of Ser. No. 719,225, Aug. 31, 1976, abandoned.

[51] Int. Cl.$^3$ .......................... C07F 9/24; A01N 57/28
[52] U.S. Cl. ...................................... 260/926; 424/204
[58] Field of Search ........................ 260/926; 424/204

[56] References Cited

U.S. PATENT DOCUMENTS

| | | | |
|---|---|---|---|
| 4,076,809 | 2/1978 | Weir et al. | 260/926 X |
| 4,086,336 | 4/1978 | Owen et al. | 260/926 X |

FOREIGN PATENT DOCUMENTS 49-93541  9/1974  Japan ........................................ 260/926

*Primary Examiner*—Anton H. Sutto
*Attorney, Agent, or Firm*—Harry H. Kline

[57] ABSTRACT

There are provided substituted p-phenylene bis[imino(thiocarbonyl)] diphosphoramidic acid esters, a method for the preparation of said esters and unsubstituted derivatives thereof and a method for controlling helminths in warm-blooded animals by administering to said animals an anthelmintically effective amount of said unsubstituted or substituted p-phenylene bis[imino(thiocarbonyl)] diphosphoramidic acid ester.

17 Claims, No Drawings

P-PHENYLENE BIS[IMINO(THIOCARBONYL)] DIPHOSPHORAMIDIC ACID ESTERS AS ANTHELMENTIC AGENTS

This application is a continuation-in-part of copending application, Ser. No. 903,293, filed May 5, 1978, which in turn is a continuation-in-part application of Ser. No. 819,304, filed July 27, 1977, which in turn is a continuation-in-part of the parent application, Ser. No. 719,225, filed Aug. 31, 1976, all now abandoned.

BACKGROUND OF THE INVENTION

Certain tetraalkyl esters of {[(o-phenylene)bis[imino(-thiocarbonyl)]}diphosphoramidic acid are disclosed in a Japanese patent application, the abstract of which has appeared in Chemical Abstracts at Volume 82, page 107520g. The application, Japanese No. 007108, filed 01/17/73 was published Sept. 5, 1974, No. 74-93541, filed by Ube Industries, Ltd., assigned to Institute of Physical and Chemical Research. The disclosed esters are said to be effective fungicidal agents. However, the claimed compounds per se of the present invention are not described therein; nor is it anticipated or suggested that the above-said compounds would be effective for the control of helminths in warm-blooded animals. Phosphonothioureides are also disclosed in U.S. Pat. Nos. 4,076,809 and 4,086,336. These disclosures, however, do not claim or disclose para-phenylene bis-[imino(thiocarbonyl)] diphosphoramidates esters as anthelmintic agents. Furthermore, it is indicated in U.S. Pat. No. 4,086,336 that the preferred compounds are ortho-phenylene compounds. Several of these phosphonoureides are found to be toxic and less effective than the para-phenylene derivatives in a series of anthelmintic assays.

SUMMARY OF THE INVENTION

The present invention relates to substituted phenylene bis[imino(thiocarbonyl)] diphosphoramidic acid esters represented by the formula:

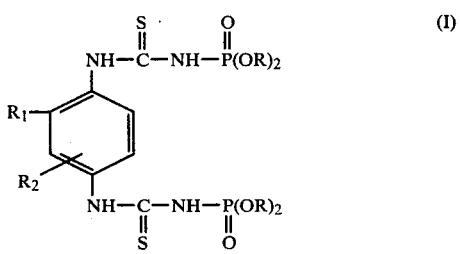

wherein R is alkyl $C_1$–$C_4$; $R_1$ is alkyl $C_1$–$C_4$ or halogen, such as chlorine, bromine, iodine, $R_3O$, $CF_3$, $R_3S$; $R_2$ is hydrogen, methyl or chloro; $R_3$ is alkyl $C_1$–$C_4$, benzyl, or phenyl.

A more preferred group of compounds represented by formula (I) are those wherein R is alkyl ($C_1$–$C_4$), $R_1$ represents a member selected from the group consisting of methyl, methoxy, benzyloxy, phenoxy, methylthio, n-propylthio, benzylthio, phenylthio, chloro, bromo, iodo and $CF_3$; $R_2$ is hydrogen, methyl or chloro.

The most preferred compounds of formula (I) compounds are those of the structure;

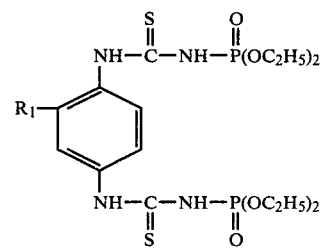

wherein $R_1$ is methoxy phenoxy, methylthio, n-propylthio, benzylthio, phenylthio, chloro, bromo, iodo or $CF_3$.

The invention further relates to a method for controlling helminths in domestic, farm, zoo, fur-bearing and laboratory animals by administering to said animals an anthelmintically effective amount of a diphosphoramidate compound having the hereinabove defined structure wherein the several substituents represented by each of the Rs are defined above, wherein $R_1$ also includes hydrogen.

In general, the diphosphoramidate compounds of the present invention depicted by formula (I) above, as well as those wherein $R_1$ is hydrogen or alkyl ($C_1$–$C_4$) are highly effective anthelmintic agents when administered orally or by subcutaneous or intraruminal injection to domestic, farm, zoo, fur-bearing or laboratory animal. They are particularly useful for treating domestic and farm animals such as dogs, cats, sheep, rabbits, cattle, horses, swine and goats and are highly effective against a wide variety of helminths, including those of the genera Hymenolepis, Aspicularis, Ascaris, Haemonchus, Ostertagia, Trichostrongylus, Ancylostoma, Dipylidium, Uncinaria, Trichuris, Toxascaris, Toxocara, and Taenia, which infest and debilitate vast numbers of these animals annually. Moreover, the compounds of this invention are especially unique in their effectiveness against tapeworms, such as Taenia, Hymenolepis and Dipylidium.

It has been unexpectedly found that the diphosphoramidate compounds of this invention will provide effective helminth control when administrated to said animals in a single dose at dosage levels of from 0.5 mg/kg to 100 mg/kg of animal body weight and, preferably, between 2.5 mg/kg and 50 mg/kg, of animal body weight.

The said compounds can also be administered to animals on a continuing basis incorporated in the diet of the animals at drug levels between 0.006% and 0.2%, by weight, of the feed and, preferably, between 0.0125% and 0.05%, by weight, of the feed. For incorporation in the feed, the active compounds herein can be formulated as a premix or supplement containing from about 5% to 25%, by weight, of said compounds. The remainder of the premix or supplement is usually a mixture of animal nutrients, e.g. soybean meal, groun grain, corn meal, fermentation residues, vegetable oils and the like. The premix or supplement is added to the animal feed in sufficient quantity to provide a concentration of active compounds required for controlling the helminth infection of said animals.

For single dose administration the compounds may be formulated as boluses, tablets, pills, injectables and the like, using pharmaceutically acceptable diluents, binders, lubricants, solvents and the like, e.g. dicalcium phosphate starch, lactose, magnesium stearate, vegetable gums, isotonic saline solution and the like.

Advantageously, the anthelmintically active phenylene bis(iminothiocarbonyl) diphosphoramidic acid esters of the present invention can be prepared by reacting 2 moles of cyanatidate of the formula:

wherein R is alkyl ($C_1$–$C_4$) such as methyl, ethyl, n-propyl, isopropyl, n-butyl, or sec-butyl with a mole of p-phenylenediamine having the formula:

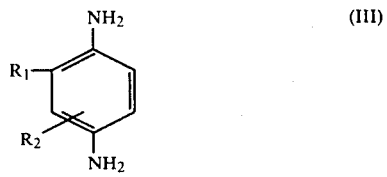

wherein $R_1$ is hydrogen, alkyl ($C_1$–$C_4$), chlorine, bromine, iodine, $R_3O$, or $CF_3$, or $R_3$-S; $R_3$ is alkyl ($C_1$–$C_4$), benzyl or phenyl; $R_2$ is hydrogen, methyl or chloro. The reaction is conducted in the presence of an organic solvent at a temperature ranging between about 0° C. and 100° C. The overall reaction can be illustrated as follows:

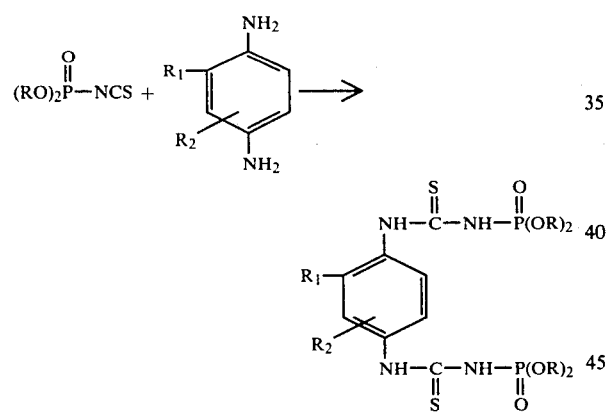

wherein R, $R_1$ and $R_2$ are as defined above.

Suitable solvents in which this reaction can be conducted include chlorinated hydrocarbons such as chloroform, methylene chloride and ethylene dichloride; aromatics such as benzene and toluene; dialkyl or cyclic ethers, polyethers; nitriles such as acetonitrile and ketones such as acetone, diethylketone and the like.

In order to facilitate a further understanding of the invention, the following examples are presented primarily for the purpose of illustrating certain more specific details thereof. The invention is not to be deemed limited thereby except as defined in the claims. Unless otherwise noted, all parts are by weight.

EXAMPLE 1

Preparation of tetraethyl-{(o-phenylene)bis[imino(thio)carbonyl]}diphosphoramidate A solution of 39.0 g of diethyl phosphoroisothiocyanatidate in 100 ml of chloroform is cooled in an ice bath. Into this cold solution is slowly stirred 10.8 g of o-phenylenediamine. A very mild exotherm is noted. The homogeneous dark brown solution is stirred for several minutes in the ice bath, and then is allowed to warm to room temperature. The solution then is heated at reflux for one hour, cooled, and the solvent is evaporated under reduced pressure. The residual pasty solids (m.p. 123° to 127° C.) are suspended in ethyl acetate and filtered to yield 40.4 g (81%) of white crystals with m.p. 134.5°–135.5° C. (decomp.). Recrystallization from 300 ml of ethylene dichloride yields 32.5 g (65%) of large, colorless crystals with m.p. 135.5°–136.5° C. Infrared and proton magnetic reasonance spectra confirm the indentity of the material.

Analysis: calculated for $C_{16}H_{28}N_4O_6P_2S_2$: C, 38.55; H, 5.66; P, 12.43. Found: C, 38.72; H, 5.84; P, 12.12.

Substituting dimethyl phosphoroisothiocyanatidate or diisopropyl phosphoroisothiocyanatidate for diethyl phosphoroisothiocyanatidate in the reaction above, there are obtained tetra-methyl-{o-phenylene)bis[imino(thiocarbonyl)]}diphosphoramidate, tetraisopropyl-{(o-phenylene)bis[imino(thiocarbonyl)]}diphosphoramidate, respectively.

EXAMPLE 2

Preparation of Tetraethyl-{(2-methoxy-p-phenylene)bis[imino(thiocarbonyl)]}diphosphoramidate 2-Methoxy-p-phenylenediamine-$H_2SO_4$ (100 g) is stirred for an hour in a solution containing 42 g of NaOH in 550 ml of $H_2O$. The diamine is extracted eleven times successively with 200 ml of $CH_2Cl_2$ and the combined extracts are dried over $MgSO_4$. The extract is filtered and evaporated to dryness in vacuo to afford 43 g (79.6% recovery) of 2-methoxy-p-phenylenediamine. The solid diamine then is added to diethoxyphosphinyl isothiocyanate (or diethyl phosphoroisothiocyanatidate prepared by stirring 134.4 g of diethyl phosphorchloridate with 66 g of dry NaSCN in 150 ml of $CH_2Cl_2$) in $CH_2Cl_2$. An additional 300 ml of $CH_2Cl_2$ is added and after 23 hours at ambient temperature, the mixture is warmed to reflux temperature on a steam bath. The mixture is cooled and 400 ml of water is added and after shaking, the organic phase is separated. The organic phase is treated with charcoal and evaporated to dryness to afford a brown residue. This residue is stirred in 100 ml of acetone/240 ml of pentane and filtered to give 118 g (72%) of the title compound. The overall yield including the isolation of the diamine is 57.6%.

Extraction of 2-methoxy-p-phenylenediamine from neutralization of 1 mole of its sulfuric acid salt using 800 ml of $CH_2Cl_2$ in a single extraction affords 93 g (67%) of this diamine.

EXAMPLE 3

The following compounds "D" are prepared by the method of Example 1, wherein

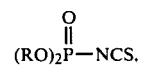

is caused to react with the appropriate p-phenylenediamine utilizing toluene in lieu of chloroform to recover a white solid in good yield.

| "D" Product | m.p. (in °C.) |
|---|---|
| (C₂H₅O)₂P(=O)—NH—C(=S)—NH—C₆H₄—NH—C(=S)—NH—P(=O)(OC₂H₅)₂ | 143–145 |
| (C₂H₅O)₂P(=O)—NH—C(=S)—NH—C₆H₃(Cl)—NH—C(=S)—NH—P(=O)(OC₂H₅)₂ | 148–149 |
| (C₂H₅O)₂P(=O)—NH—C(=S)—NH—C₆H₃(OCH₃)—NH—C(=O)—NH—P(=S)(OC₂H₅)₂ | 143–144 |
| 2-CH₃-1,4-C₆H₃[NH—CS—NH—P(=O)(OC₂H₅)₂]₂ | 156.5–157.5 |
| 2-(n-C₃H₇S)-1,4-C₆H₃[NH—C(=S)—NH—P(=O)(OC₂H₅)₂]₂ | 126–129 |
| 2-(C₆H₅S)-1,4-C₆H₃[NH—C(=S)—NH—P(=O)(OC₂H₅)₂]₂ | 141–143 |
| 2-(C₆H₅O)-1,4-C₆H₃[NH—C(=S)—NH—P(=O)(OC₂H₅)₂]₂ | 130–133 |
| 2-(C₆H₅CH₂S)-1,4-C₆H₃[NH—C(=S)—NH—P(=O)(OC₂H₅)₂]₂ | 129–133 |
| 2-(CH₃S)-1,4-C₆H₃[NH—C(=S)—NH—P(=O)(OC₂H₅)₂]₂ | 138–141 |
| 2,5-(CH₃)₂-1,4-C₆H₂[NH—C(=S)—NH—P(=O)(OC₂H₅)₂]₂ | 167–168 |

-continued

| "D" Product | m.p. (in °C.) |
|---|---|
| 3-iodo-1,4-phenylene bis(N'-diethoxyphosphinyl thiourea) | 149–150 |
| 2-chloro-5-methoxy-1,4-phenylene bis(N'-diethoxyphosphinyl thiourea) | 148–151 |
| 2-chloro-5-methyl-1,4-phenylene bis(N'-diethoxyphosphinyl thiourea) | 152–155 |
| 2,5-dichloro-1,4-phenylene bis(N'-diethoxyphosphinyl thiourea) | 164–165 |
| 2-chloro-5-phenylthio-1,4-phenylene bis(N'-diethoxyphosphinyl thiourea) | 143–146 |
| 2-trifluoromethyl-1,4-phenylene bis(N'-diethoxyphosphinyl thiourea) | 151–152 |
| 2,3-dichloro-1,4-phenylene bis(N'-diethoxyphosphinyl thiourea) | 150–153 |
| 2-chloro-1,4-phenylene bis(N'-diisopropoxyphosphinyl thiourea) | 150–152 |

(Note: structural drawings present; textual names above are approximations of the depicted structures.)

| "D" Product | m.p. (in °C.) |
|---|---|
| 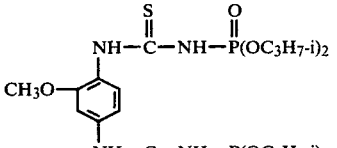 | 149–152 |
| 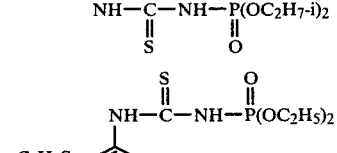 | — |
| 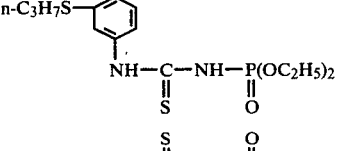 | 133–134 |
| 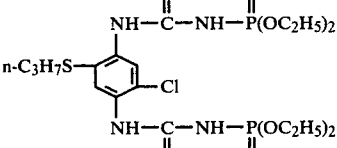 | 134–137 |
| 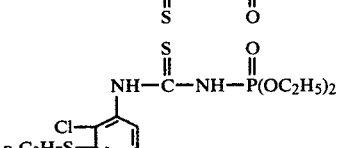 | 142–145 |
| 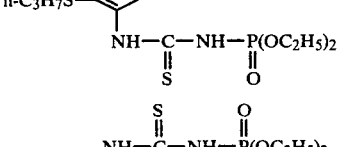 | 155–156 |
| 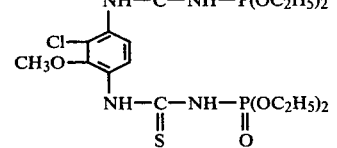 | 158–160 |
| 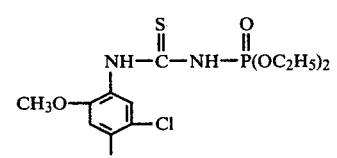 | 178–179 |

-continued

| "D" Product | m.p. (in °C.) |
|---|---|
| 2,6-dimethyl-phenylene bis structure | — |
| 2-bromo-phenylene bis structure | 152–152.5 |
| 2-phenoxy-5-chloro-phenylene bis structure | 141–142 |
| 2-methylthio-5-methyl-phenylene bis structure | 142–145 |
| 2-chloro-5-methyl-phenylene bis structure | 162–164 |
| 2-benzylthio-phenylene bis structure | 129–133 |

EXAMPLE 4

Preparation of
Tetraethyl-{[(2-chloro-5-phenylthio)p-phenylene]bis-[imino(thiocarbonyl)]}diphosphoramidate A solution of 2-chloro-5-phenylthio-p-phenylenediamine (7.8 g) in methylene chloride (16 ml) is stirred and 26 ml of a solution of

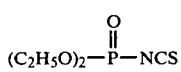

in methylene chloride (195 g in 350 ml of methylene chloride) is added. The mixture is heated at reflux for one hour, then evaporated to dryness and the residue warmed at 50° C. for two hours. Acetone (60 ml) is added to the residue and the mixture is stirred and after a period of time, a white precipitate is formed. The mixture is then diluted with pentane (30 ml), the solid collected and washed with acetone, to afford 10.4 g of title compound, m.p. 143°–144° C.

Similarly, the following compounds are prepared using the appropriately substituted diamines:

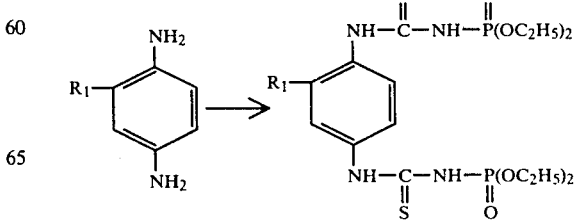

wherein $R_1$ is $CH_3S$, $C_2H_5S$, $i-C_3H_7S$, $n=C_4H_9S$, benzylthio, phenylthio, F, $C_2H_5O$, $n-C_3H_7O$, $n-C_4H_9O$, benzyloxy, phenoxy, $C_2H_5$ and $n-C_4H_9$.

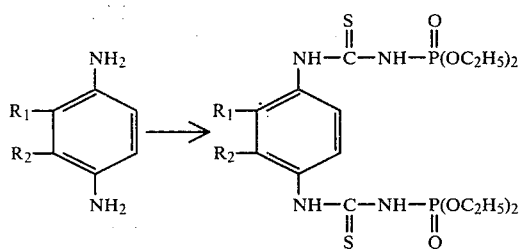

wherein $R_1$ is Cl; and $R_2$ is Cl, $CH_3O$, $C_2H_5O$, $n-C_3H_7O$, $n-C_4H_9O$, phenoxy, benzyloxy, $CH_3S$, $C_2H_5S$, $n-C_3H_7S$, $n-C_4H_9S$, phenylthio or benzylthio.

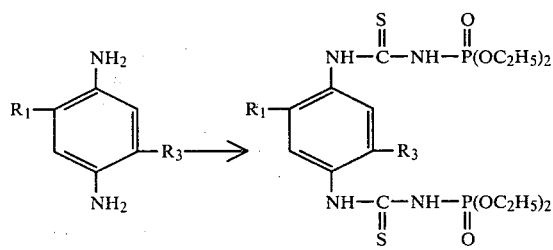

wherein $R_3$ is Cl; $R_1$ is $CH_3S$, $C_2H_5S$, $n-C_3H_7S$, $n-C_4H_9S$, benzylthio, $CH_3O$, $C_2H_5O$, $n-C_3H_7O$, $i-C_3H_7O$, $n-C_4H_9O$, benzyloxy and phenoxy.

EXAMPLE 5

Preparation of Diethoxyphosphinyl Isothiocyanate

To a mixture of 8.02 g of dry sodium thiocyanate in 100 ml of dry toluene at 0° C., under a nitrogen atmosphere is added 13.1 ml (16.6 g) of diethyl phosphorchloridate dropwise with stirring. The mixture is warmed to ambient temperature and stirred 20 hours. The mixture is filtered through a pad of Celite and the pad is washed with two 50 ml portions of toluene. The filtrate is washed with 50 ml of ice cold 10% sodium bicarbonate solution, 50 ml of ice water and dried over anhydrous magnesium sulfate. The mixture is filtered and the filtrate used without further purification is subsequent reaction.

EXAMPLE 6

Preparation of 4-Nitro-3-(n-propylthio)aniline

In 50 ml of dry dimethylformamide, 5 grams of 3-chloro-4-nitroaniline, 6.9 grams of potassium carbonate, and 2.73 ml of n-propyl mercaptan are stirred under nitrogen atmosphere for 5 minutes and then heated at 87° C. for 20.5 hours. An additional 0.5 ml of propyl mercaptan is then added and the mixture is heated 2 hours at 105° C. The mixture is cooled, poured into 400 ml of $H_2O$ with stirring to afford the gold-colored product (6 grams), melting at 68°–72° C.

EXAMPLE 7

Preparation of 3-Methylthio-4-nitroaniline

A mixture of dry dimethylformamide (150 ml) and potassium carbonate (12.0 g) is stirred and methyl mercaptan is introduced as a gas for 45 minutes. After stirring for another 45 minutes, 3-chloro-4-nitroaniline (10.0 g) is added. The mixture is stirred and heated at 120°–130° C. for 18 hours. It is then cooled and poured into water (1 liter), the precipitate is collected and recrystallized from methanol to afford 8 grams of 3-methylthio-4-nitroaniline, m.p. 178°–182° C.

Similarly, 3-ethylthio-4-nitroaniline, 3-n-propylthio-4-nitroaniline, 3-isopropylthio-4-nitroaniline, 3-n-butylthio-4-nitroaniline and 3-benzylthio-4-nitroaniline are each prepared employing the corresponding mercaptan in excess.

EXAMPLE 8

In a Paar hydrogenation bottle, 7 g of 4-nitro-3-(n-propylthio)aniline, 7 g of 5% palladium/carbon, and 5.32 ml of concentrated hydrochloric acid in 200 ml of absolute ethanol are shaken under 3.36 kg/cm² pressure for 50 minutes (2.80 kg/cm² pressure). The mixture is filtered through Celite and the filter cake is washed with 150 ml of ethanol. The combined wash and filtrate is evaporated to dryness in vacuo to afford a white solid, which is stirred in 50 ml of cold acetone and collected to yield 5.2 g of n-propylthio-p-phenylenediamine (m.p. 213°–225° C.).

EXAMPLE 9

Preparation of 2-Methylthio-p-phenylenediamine

In a Paar hydrogenation bottle, a mixture of 3-methylthio-4-nitroaniline (7.7 g), 5% Pd/C catalyst (8.0 g), concentrated hydrochloric acid (7 ml) and ethanol (200 ml) is treated with hydrogen at 3.43 kg/cm² for 45 minutes (until 0.8 kg/cm² Hydrogen is absorbed). The mixture is filtered through diatomaceous earth and the filtrate evaporated to dryness afford 3-methylthio-p-phenylenediamine hydrochloride. The salt is dissolved in water, the solution made alkaline (pH 9–10) with 50% sodium hydroxide and the diamine extracted with methylene chloride (3×150 ml). The combined extracts are dried over magnesium sulfate and evaporated to dryness to afford 4.75 g of title product, a brown solid, which is used as is.

In the same manner, 3-ethylthio-, 3-n-propylthio-, 3-isopropylthio-, 3-n-butylthio- and 3-benzylthio-4-nitroaniline are reduced to afford 2-ethylthio-, 2-n-propylthio-, 2-isopropylthio-, 2-n-butylthio and 2-benzylthio-p-phenylenediamine, respectively, in good yield.

EXAMPLE 10

Preparation of 2-Iodo-4-nitroaniline

A solution of iodine monochloride (23.54 g) in acetic acid (50 ml) is added dropwise over an hour to a stirred solution of p-nitroaniline (20 g). After stirring for another hour, the dark mixture is poured into water (1 liter), the precipitated yellow solid is collected and dried to afford 41.15 g title product, m.p. 90°–95° C.

EXAMPLE 11

Preparation of 2-Iodo-p-phenylenediamine

A mixture of concentrated hydrochloric acid (150 ml) and 2-iodo-4-nitroaniline (30.0 g) is stirred and warmed to 45°–50° C. A solution of stannous chloride dihydrate (90.0 g) in concentrated hydrochloric acid (110 ml) is added while maintaining the reaction temperature at 65°–70° C. After the addition is completed, the mixture is cooled in an ice bath and 50% sodium hydroxide (250 ml) is added slowly. The mixture is filtered and the isolated damp solid is stirred in 600 ml water at reflux. The solution is decolorized with charcoal, filtered and cooled to afford 5.55 g of title compound, m.p. 95°–99° C.

EXAMPLE 12

Preparation of 2-Chloro-4-nitro-6-methoxyaniline

A mixture of concentrated hydrochloric acid (250 ml), water (250 ml) and 2-methoxy-4-nitroaniline (48.76 g) is stirred at 47° C. and 30% hydrogen peroxide (30 ml) is added. The temperature is kept at 50°–62° C. and after one hour an additional 125 ml of concentrated hydrochloric acid and 15 ml of 30% hydrogen peroxide are added. After 45 minutes at 45°–48° C., the mixture is cooled and the precipitate collected to yield 54 g of a brown solid. This material is purified by dry column chromatography using silica and 1:1 hexane/toluene eluent to afford 11.0 g of title product, m.p. 114°–115° C.

Similarly, 2-chloro-4-nitro-6-methylaniline, m.p. 154°–159° C., is prepared from 2-methyl-4-nitroaniline.

Using the corresponding 6-alkyl-4-nitroaniline, the following are also prepared: 2-chloro-4-nitro-6-ethylaniline and 2-chloro-4-nitro-6-n-butylaniline.

EXAMPLE 13

Preparation of 2,3-Dichloro-4-nitroaniline

A solution of 2,3-dichloroaniline (162.0 g) in p-toluenesulfonyl chloride (190.7 g) is heated at 100° C. for one hour allowing the temperature to rise to 115° C. with the exotherm. The thick mixture is then cooled to 50° C. and pyridine (250 ml) is added carefully. The reaction mixture exotherms to 150° C. After stirring for one hour the mixture is cooled and poured into water (2.5 liter). The precipitated solid is collected and dried to yield 301 g of tosylamide, m.p. 112°–118° C.

The tosylamide (250 g) is added to 70% nitric acid (71.15 g) and the mixture warmed on a steam bath and is cooled after the evolution of red fumes stops. The mixture is then stirred with 1 liter of water and the solid collected. The nitrated product is recrystallized from methanol to afford 137.2 g solid, m.p. 139°–144° C. This crude product is dissolved in concentrated sulfuric acid (150 ml) and the solution warmed on a steam bath for 35 minutes. The solution is cooled and poured into two liters of water, the precipitate is collected and dried to afford 77.1 g of title compound, m.p. 170°–174° C.

EXAMPLE 14

Preparation of 2-Chloro-3-methoxy-4-nitroaniline

A solution of 2,3-dichloro-4-nitroaniline (25 g) and sodium methoxide (25 g) in methanol (250 ml) is stirred and heated at reflux under a nitrogen atmosphere for 5.5 hours. The reaction mixture is poured into water (1.5 l), the precipitated yellow solid is collected and dried. This material is purified by chromatography on silica gel using 1:1 hexane/ether eluent. The eluents are collected and evaporated to dryness to afford 13 g of title compound, m.p. 118°–123° C.

Similarly, 2,5-dichloro-4-nitroaniline is allowed to react with methoxide ion to afford 2-chloro-4-nitro-5-methoxyaniline, m.p. 150°–152° C. Also by allowing 2,3-dichloro-4-nitroaniline to react with sodium ethoxide, sodium propoxide, sodium butoxide and sodium benzyloxide, 3 ethoxy-, 3-propoxy-, 3-isopropoxy-, 3-butoxy- and 3-benzyloxy-4-nitroaniline are obtained.

Reaction of 2,5-dichloro-4-nitroaniline with the above alkoxides in the same manner also affords 5-ethoxy-, 5-propoxy-, 5-isopropoxy-, 5-n-butoxy-, and 5-benzyloxy-2-chloro-4-nitroaniline.

EXAMPLE 15

Preparation of 2-Chloro-3-methoxy-4-nitroaniline

A mixture of 2,5-dichloro-4-nitroaniline (7.0 g), phenol (3.2 g), potassium carbonate (9.7 g) and dry dimethylformamide (50 ml) is stirred and heated at 100° C. for 7.5 hours. The mixture is then poured into 500 ml of ice water and stirred. The aqueous mixture is extracted with ethyl acetate (5×200 ml), the extracts are dried and evaporated to dryness. The residual oil is stirred with methylene chloride (20 ml), the resulting solid is collected and dried to yield 3.5 g of title product, m.p. 122°–124° C.

Similarly, 2,5-dichloro-4-nitroaniline is allowed to react with n-propyl mercaptan and thiophenol in dimethylformaldehyde at 100° C. in the presence of potassium carbonate to afford 2-chloro-4nitro-5-n-propylthioaniline, m.p. 125°–127° C., and 2-chloro-4-nitro-5-phenylthioaniline, m.p. 163°–166° C.

Also in the above described manner the following products are prepared:

| Starting materials | Mercaptan | Product |
|---|---|---|
| 2,5-dichloro-4-nitroaniline + | $CH_3SH \rightarrow$ | 2-Chloro-4-nitro-5-methylthioaniline |
| | $C_2H_5SH \rightarrow$ | 2-Chloro-4-nitro-5-ethylthioaniline |
| | n-$C_4H_9SH \rightarrow$ | 2-Chloro-4-nitro-5-butylthioaniline |
| | ⟨phenyl⟩-$CH_2SH \rightarrow$ | 2-Chloro-4-nitro-5-benzylthioaniline |
| 2,3-dichloro-4-nitroaniline + | $CH_3SH \rightarrow$ | 2-Chloro-3-methylthio-4-nitroaniline |
| | $C_2H_5SH \rightarrow$ | 2-Chloro-3-ethylthio-4-nitroaniline |
| | n-$C_3H_7SH \rightarrow$ | 2-Chloro-3-propylthio-4-nitroaniline |
| | n-$C_4H_9SH \rightarrow$ | 2-Chloro-3-n-butylthio-4-nitroaniline |

| Starting materials | Mercaptan | Product |
|---|---|---|
| 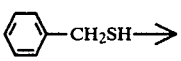 | thiophenol⟶ | 2-Chloro-3-phenylthio-4-nitroaniline |
| | ⟨◯⟩—CH₂SH⟶ | 2-Chloro-3-benzylthio-4-nitroaniline |

EXAMPLE 16

Preparation of 2-chloro-5-n-propylthio-p-phenylenediamine

A mixture of 2-chloro-4-nitro-5-n-propylthioaniline (7.0 g) and concentrated hydrochloric acid (40 ml) is warmed to 65°–75° C. and a solution of stannous chloride dihydrate (30 g) in concentrated hydrochloric acid (40 ml) is added dropwise. After 2.5 hours, the mixture is cooled and 50% aqueous sodium hydroxide (80 ml) is added. The mixture is extracted with 1 liter methylene chloride, the extract dried over magnesium sulfate and evaporated to dryness to afford 4.8 g of product, a brown oil, which is used in subsequent reactions without further purification.

Similarly, 2-chloro-4-nitro-5-phenoxyaniline is reduced to give 2-chloro-5-phenoxy-p-phenylenediamine, 2-chloro-4-nitro-5-phenylthioaniline to give 2-chloro-5-phenyl-thio-p-phenylenediamine, 2-chloro-4-nitro-5-methoxyanilino to give 2-chloro-5-methoxy-p-phenylenediamine, and 2,5-di-chloro-4-nitroaniline to give 2,5-dichloro-p-phenylenediamine.

The above procedure is also used to prepare the following phenylenediamines, wherein the starting nitroanilines are described above.

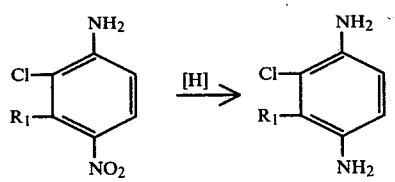

wherein $R_1$ is $CH_3S$, $C_2H_5S$, $n-C_3H_7S$, $n-C_4H_9S$, phenylthio, benzylthio, $CH_3O$, $C_2H_5O$, $n-C_3H_7O$, 3-i-$C_3H_7O$, $n-C_4H_9O$, phenoxy and benzyloxy; and

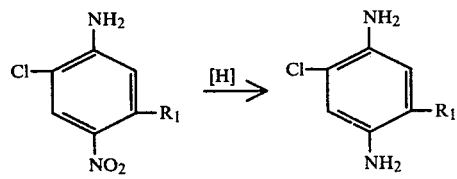

wherein $R_1$ is $CH_3S$, $C_2H_5S$, $n-C_4H_9S$, benzylthio, $CH_3O$, $C_2H_9O$, $n-C_3H_7O$, $i-C_3H_7O$, $n-C_4H_9O$ and benzyloxy.

EXAMPLE 17

Preparation of 2-n-Propoxy-p-phenylenediamine

A mixture of 2,5-dinitrophenol (10 g), potassium carbonate (15 g) and acetone (100 ml) is stirred and n-propyl bromide (13.36 g) added to the mixture. The mixture is stirred at room temperature for 3 hours and then heated at reflux for 16 hours. More n-propyl bromide (6.68 g) is then added and refluxing continued for 96 hours. The mixture is filtered and the filtrate evaporated to dryness to afford a dark brown solid. This material is stirred with water (300 ml) and filtered. Recrystallization from methanol yields 8.9 g of 1-n-propoxy-2,5-dinitrobenzene, m.p. 52°–54° C. This compound (8.4 g) is reduced with hydrogen in a pressure vessel in the presence of methanol (250 ml) and 5% Pd/C catalyst (0.85 g); starting pressure: 3.36 kg/cm², final pressure: 2.52 kg/cm². The mixture is filtered and evaporated to dryness to afford 6.1 g of oily title compound, which is used in subsequent reactions without further purification.

Similarly, 2-n-butoxy-p-phenylenediamine, 2-ethoxy-p-phenylenediamine are prepared using butyl iodide and ethyl iodide in the first step. Use of benzyl bromide affords 2-benzyloxy-p-phenylenediamine.

EXAMPLE 18

Efficacy of Tetraalkyl ($C_1$–$C_4$) esters of phenylenebis[imino(thiocarbonyl)]diphosphoramidate against various helminths in mice Six weeks od Swiss Webster mice are orally inoculated with *Nematospiroides dubius*, *Hymenolepis nana* and *Aspicularis tetraptera*. Eighteen days postinoculation the mice are treated with the appropriate drug diet evel for 7 days. For single oral dose (SOD) administration the compound is thoroughly mixed with 0.1% agar and orally intubated at the required dosage 22 days postinfection. Determination of efficacy is done by counting all the N. dubius in treated mice versus the control average. For H. nana and A. tetraptera the absence or presence of these parasites in treated mice is the criterion for determining activity. The data are summarized in Table I below.

Diet

The diet used in the test procedure is a standard commercial mouse chow containing meat and bone meal, dried skimmed milk, wheat germ meal, fish meal, animal liver meal, dried beet pulp, ground extended corn, oat middlings, soybean meal, dehydrated alfalfa meal, cane molasses, animal fat preserved with BHA, vitamin B-12 supplement, calcium panthotente, choline chloride, folic acid, riboflavin supplement, brewer's dried yeeast, thiamine, niacin, vitamin A supplement, D activated plant sterol, vitamin E supplement, dicalcium phosphate, iodized salt, ferric ammonium citrate, iron oxide, manganous oxide, cobalt carbonate, copper oxide and zinc oxide; and the desired level of test compound.

TABLE I

Mouse/Helminth Evaluation

| Compound | in % | N. dubius | A. tetraptera | H. nana |
|---|---|---|---|---|

Structure 1:

$$\text{Ar}\left[\begin{array}{l}\text{NH-C(=S)-NH-P(=O)(SC}_2\text{H}_5\text{)(OC}_2\text{H}_5\text{)} \\ \text{NH-C(=S)-NH-P(=O)(SC}_2\text{H}_5\text{)(OC}_2\text{H}_5\text{)}\end{array}\right]$$

where Ar is a phenyl ring with -OCH$_3$ substituent

| | 0.1 | Inactive | NT** | Inactive |
| | 0.05 | Inactive | NT | Inactive |
| | 0.025 | Inactive | NT | Inactive |

(disclosed in U.S. Pat. No. 4,086,336)

Structure 2 (ortho-phenylene bis-urea phosphonate, O,S isomers):

| | 0.05 | Inactive | Inactive | Inactive |
| | 50 | Inactive | Inactive | Inactive |

(disclosed in U.S. Pat. No. 4,076,809)

Structure 3:

| | 0.05 | Inactive | Active | Inactive |
| | 50 | Inactive | Inactive | Inactive |

(disclosed in U.S. Pat. No. 4,076,809)

Structure 4:

| | 0.05 | Inactive | Inactive | Inactive |
| | 50 | Inactive | Inactive | Inactive |

(disclosed in U.S. Pat. No. 4,076,809)

Compound of the Present Invention

General structure:

$$\begin{array}{c}\text{NH-C(=S)-NH-P(=O)(OR)}_2 \\ \text{(phenyl ring with R}_1, R_2\text{)} \\ \text{NH-C(=S)-NH-P(=O)(OR)}_2\end{array}$$

| R$_1$ | R$_2$ | R | Medication* in % | N. dubius | A. tetraptera | H. nana |
|---|---|---|---|---|---|---|
| Cl | H | C$_2$H$_5$ | 0.05 | Inactive | Active | Active |
| | | | 50 | Inactive | Active | Inactive |
| CH$_3$O | H | C$_2$H$_5$ | 0.1 | Inactive | NT | Active |
| | | | 0.05 | Inactive | Active | Active |
| | | | 0.025 | Inactive | NT | Active |
| | | | 50 | Inactive | Inactive | Inactive |
| CH$_3$ | H | C$_2$H$_5$ | 0.05 | Inactive | Active | Active |
| | | | 50 | Inactive | Active | Active |
| C$_6$H$_5$CH$_2$S- | H | C$_2$H$_5$ | 0.05 | Inactive | Active | Active |
| | | | 50 | Inactive | NT | Inactive |
| C$_6$H$_5$O- | H | C$_2$H$_5$ | 0.05 | Inactive | Active | Active |
| | | | 50 | Inactive | Active | Active |
| CH$_3$S | H | C$_2$H$_5$ | 0.05 | Inactive | Active | Active |
| | | | 50 | Inactive | Active | Active |
| CH$_3$O | H | i-C$_3$H$_7$ | 0.05 | Inactive | Active | Active |
| | | | 50 | Inactive | Inactive | Active |
| Cl | H | i-C$_3$H$_7$ | 0.05 | Inactive | Active | Active |

TABLE I-continued

Mouse/Helminth Evaluation

| | | | | | | |
|---|---|---|---|---|---|---|
| | | | 50 | Inactive | Active | Active |
| CF$_3$ | H | C$_2$H$_5$ | 0.05 | Inactive | Active | Active |
| | | | 50 | Inactive | Active | Inactive |
| CH$_3$ | 5-CH$_3$ | C$_2$H$_5$ | 0.05 | Inactive | Active | Active |
| | | | 50 | Inactive | Active | Active |
| I | H | C$_2$H$_5$ | 0.05 | Inactive | Active | Active |
| | | | 50 | Inactive | Inactive | Active |
| Br | H | C$_2$H$_5$ | 0.05 | Inactive | Inactive | Active |
| | | | 50 | Inactive | Active | Inactive |
| CH$_3$O | 6-Cl | C$_2$H$_5$ | 0.05 | Inactive | Active | Inactive |
| | | | 50 | Inactive | Inactive | Active |
| Cl | 5-Cl | C$_2$H$_5$ | 0.05 | Inactive | Active | Active |
| | | | 50 | Inactive | Active | Inactive |
| C$_6$H$_5$—S | 5-Cl | C$_2$H$_5$ | 0.05 | Inactive | Active | Active |
| | | | 50 | Inactive | Inactive | Inactive |
| CH$_3$ | 3-CH$_3$ | C$_2$H$_5$ | 0.05 | Inactive | Active | Active |
| | | | 50 | Inactive | Active | Inactive |
| —S | H | C$_2$H$_5$ | 0.05 | Inactive | NT | Active |
| | | | 50 | Inactive | Inactive | Active |
| —O | 5-Cl | C$_2$H$_5$ | 0.05 | Inactive | Active | Active |
| | | | 50 | Inactive | Active | Inactive |
| CH$_3$O | 5-CH$_3$ | C$_2$H$_5$ | 0.05 | Inactive | Active | Active |
| | | | 50 | Inactive | Active | Inactive |
| CH$_3$ | 5-Cl | C$_2$H$_5$ | 0.05 | Inactive | Active | Active |
| | | | 50 | Inactive | — | Inactive |
| n-C$_3$H$_7$S | 5-CH$_3$ | C$_2$H$_5$ | 0.05 | Inactive | Active | Active |
| | | | 50 | Inactive | Active | Inactive |
| CH$_3$O | 3-Cl | C$_2$H$_5$ | 0.05 | Inactive | Active | Active |
| | | | 50 | Inactive | Active | Inactive |
| n-C$_3$H$_7$S | 3-Cl | C$_2$H$_5$ | 0.05 | Inactive | Active | Active |
| | | | 50 | Inactive | Active | Inactive |
| n-C$_3$H$_7$S | 5-Cl | C$_2$H$_5$ | 0.05 | Inactive | Active | Active |
| | | | 50 | Inactive | Inactive | Inactive |
| Cl | 3-Cl | C$_2$H$_5$ | 0.05 | Inactive | Active | Active |
| | | | 50 | Inactive | Active | Inactive |
| Cl | 6-CH$_3$ | C$_2$H$_5$ | 0.05 | Inactive | Active | Active |
| | | | 50 | Inactive | Active | Active |

*% = Concentration in diet. Integers = mg/kg single oral dose
**NT = not tested

EXAMPLE 19

Evaluation (Efficacy) Test in Sheep

Lambs are experimentally inoculated with *Haemonchus contortus* (H.c.), *Ostertagia circumcincta* (O.c.) and *Trichostrongylus colubriformis* (T.c.) species. At patency of the parasites the lambs are treated with 12.5, 25 or 50 mg/kg of body weight with the compound under test, administered as a single oral dose (SOD). At necropsy 6 days post treatment, abomasa and small intestines of treated and untreated control lambs were removed. Abomasa were processed by digestion (HCl & pepsin) techniques. Small intestines were slit and worms were recovered by rinsing the intestinal wall. After sieving the abomasa digest and intestinal wash, aliquot were taken and worms counted. The individual worm counts were averaged by species for control and treatment groups and the percent efficacy calculated from the formula:

$$\% \text{ Efficacy} = \frac{\text{Av. No. in Controls} - \text{Av. in treated}}{\text{Av. No. in Controls}} \times 100$$

TABLE II

| | sheep/Helminth Evaluation | | | | |
|---|---|---|---|---|---|
| | Oral Dose | No. of | % Efficacy Against | | |
| COMPOUND | mg/kg | Sheep | *H. contortus* | *O. circumcineta* | *T. colubriformis* |
| 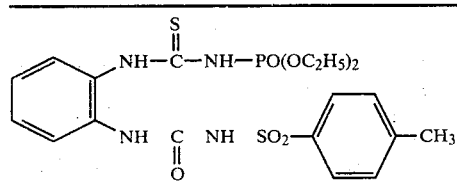 | 50 | 4 | 97.8 | 44.2 | 48.2 |

Uredofos (Sansalid ®)
Disclosed in U.S. Pat. No. 4,076,809

TABLE II-continued

| COMPOUND | sheep/Helminth Evaluation | | % Efficacy Against | | |
|---|---|---|---|---|---|
| | Oral Dose mg/kg | No. of Sheep | H. contortus | O. circumcincta | T. colubriformis |
| NH—C(=S)—NH—PO(OC$_2$H$_5$)$_2$, phenyl-Cl, NH—C(=S)—NH—PO(OC$_2$H$_5$)$_2$ | 50 | 4 | 100 | 92.8 | 87.1 |
| | 25 | 4 | 99.6 | 74 | 22.4 |
| NH—C(=S)—NH—PO(OC$_2$H$_5$)$_2$, phenyl-OCH$_3$, NH—C(=S)—NH—PO(OC$_2$H$_5$)$_2$ | 50 | 4 | 100 | 97.8 | 91.5 |
| | 25 | 4 | 100 | 85.4 | 75.4 |
| | 12.5 | 4 | 100 | 48.2 | 16.5 |
| NH—C(=S)—NH—PO(OC$_2$H$_5$)$_2$, phenyl, NH—C(=S)—NH—PO(OC$_2$H$_5$)$_2$ | 50 | 4 | 100 | 99.5 | 94 |

EXAMPLE 20

Evaluation (Efficacy) Test in Rabbits

New Zealand white rabbits are inoculated with 2000 *Trichostrongylus colubriformis* larvae. Twenty-one days post inoculation the rabbits are treated with the test compounds at the mg/kg body weight levels indicated in table below, administered as a single oral dose (SOD) in a gelatin capsule. Three days post treatment, the rabbits are necropsied and examined for parasites. Percent efficacy is calculated using the formula:

$$\% \text{ Efficacy} = \frac{\text{Av. No. in controls - Av. No. in treated}}{\text{Av. No. in Controls}} \times 100$$

The data obtained are reported in Table III, where it can be clearly seen that while the compounds of the present application are highly effective for the control of adult *Trichostrongylus colubriformis* in rabbits when administered as a single oral dose (in the range of 12.5 to 50 mg/kg animal body weight, a compound of the art (Japan, Kokai, 74, 135, 912) is totally ineffective at 50 mg/kg animal body weight.

TABLE III

Control of Adult *Trichostrongylus colubriformis* in Rabbits

| Compound | Dose mg/kg | % Efficacy |
|---|---|---|
| NH—C(=S)—NH—P(=O)(OC$_2$H$_5$)$_2$, phenyl, NH—C(=O)—NH—SO$_2$—phenyl—CH$_3$ | 50 | 0 |
| Reference compound: Uredofos (Sansalid ®) Disclosed in U.S. Pat. No. 4,076,809 NH—C(=S)—NH—P(=O)(OC$_2$H$_5$)$_2$, phenyl-Cl, NH—C(=S)—NH—P(=O)(OC$_2$H$_5$)$_2$ | 50 | 90 |
| | 25 | 88 |
| NH—C(=S)—NH—P(=O)(OC$_2$H$_5$)$_2$, phenyl-OCH$_3$, NH—C(=S)—NH—P(=O)(OC$_2$H$_5$)$_2$ | 50 | 87.2 |
| | 25 | 70.9 |

EXAMPLE 21

Yorkshire X Hampshire pigs (5 pigs/treatment are medicated. Medication is administered orally via gelatin capsules containing compounds set forth below in Table IV. Pigs are observed continuously for 2 hours following treatment, then at hourly intervals for 6 hours and again at 24 hours post-treatment. Pigs are maintained an additional 7 days for post-treatment observation. The following table encompasses the results obtained.

TABLE IV

Toxicity Study in Swine

| Compound | SOD mg/kg | No. of Pigs | No. of Pigs with Toxic Symptoms | Death |
|---|---|---|---|---|
| Art Compound** ortho-NH—C(=S)—NH—P(=O)(OC₂H₅)₂ benzene | 150 | 5 | 5 | 4 |
| | 100 | 5 | 5 | 0 |
| | 50 | 5 | 5 | 1 |
| ortho-Cl, para-NH—C(=S)—NH—P(=O)(OC₂H₅)₂ benzene | 250 | 5 | 5 | 1* |
| | 200 | 5 | 3 | 1 |
| | 150 | 5 | 5 | 0 |
| ortho-OCH₃, para-NH—C(=S)—NH—P(=O)(OC₂H₅)₂ benzene | 250 | 5 | 5 | 2* |
| | 200 | 5 | 5 | 0 |
| | 150 | 5 | 0 | 0 |

*Died 5–6 days after administration of drug by means of balling gun, death due to esophageal puncture - not related to medication.
**Japanese Application 0071008; filed 01/17/73, as fungicide.

EXAMPLE 22

Single Oral or Parenteral Dose to Mice

Procedure

Ten nonfasted female albino mice (Carworth Farms #1 strain) weighing between 18 and 24 grams are selected for each dose level. The animals are not identified individually but are identified by cage tags giving the cage number, sample number, dose level, route of administration, and date of dosing. The animals are weighed as they are dosed and a group mean weight is recorded for each dose level. The animals are observed several times after dosing and twice daily over a 14-day period for mortality, toxic symptons, and recovery time. At the end of the 14-day observation period the survivors are weighed and sacrificed. The weight recorded is the mean weight of the survivors from each dose level. The results are then tabulated and the $LD_{50}$ is calculated by either the time method of moving averages using tables constructed by Weil or Probit Analysis.

The compound is made up as a solution or dispersion in either normal saline plus 0.5% corn oil. The animals are dosed at a constant volume of 0.50 ml/20 g. of body weight.

In order to determine the $LD_{50}$ of a compound listed in the table below, wherein the $LD_{50}$ is believed to be approximately 300 mg/kg. In order to bracket this response, we select dosages of 1000, 500, 250, and 125 mg/kg. For a dosage of 1000 mg/kg, each 0.5 ml. of solution would then have to contain 20 mg. of compound below. For 20 ml. of this solution, 800 mg. of compound and 20 ml of corn oil or aqueous solution would be needed. The next lowest dosage level would be prepared by diluting 10 ml of the most concentrated solution of compound with 10 ml of corn oil. The same procedure is used for each of the other two concentrations. As a result, the last sample flask will contain a total of 20 ml in contrast to the 10 ml volume remaining in each of the proceding flasks.

TABLE V

$LD_{50}$ Comparison Between Ortho and Para Compounds in Mice

| Prior Art Compounds | $LD_{50}$ (mg/kg) |
|---|---|
| ortho-R, R benzene | 52 |
| Cl—, ortho-R, R benzene | 30 |
| CH₃O—, ortho-R, R benzene | 52 |

| Compounds of this Invention | |
|---|---|
| 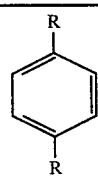 para-R, R benzene | >240 |

TABLE V-continued

LD$_{50}$ Comparison Between Ortho and Para Compounds in Mice

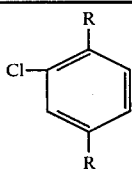

| | |
|---|---|
| | 68 |
| | 85 |

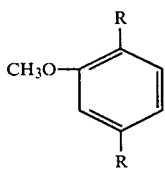

where R = NH—C(=S)—NH—P(=O)(OC$_2$H$_5$)$_2$

EXAMPLE 23

Four-month old lambs are selected from pure or crossbred Dorset, Mondal, Rambouillet, Suffolk or Hampshire breeds. They are not dosed with anthelmintics to remove any existing helminth burdens or inoculated with vaccine prior to or after administration of test drugs. Most selected lambs are free of parasites or only slightly parasitized as indicated by Stoll egg count. Lambs are acclimated to the indoor temperature (70°–75° F.) and to pelleted ration for at least one week prior to dosing and the test drugs are administered in gelatin capsules with the aid of a balling gun. Ration is not removed prior to and after dosing of drug and water is made available ad libitum. After dosing lambs are observed carefully and frequently throughout the day for symptoms or death and kept under observation for a month.

TABLE VI

Toxicity in Sheep

| COMPOUND | SOD mg/kg | Number dead/total | Symptoms Observed in Survivors |
|---|---|---|---|
| (phenyl) with ortho NH—C(=S)—NH—P(=O)(OC$_2$H$_5$)$_2$ and NH—C(=S)—NH—P(=O)(OC$_2$H$_5$)$_2$ | 50<br>100 | 1/2<br>1/2 | Salivation, rigidity, malaise, anorexia symptoms persisted for 9 days |
| Cl-(phenyl) with ortho NH—C(=S)—NH—P(=O)(OC$_2$H$_5$)$_2$ and NH—C(=S)—NH—P(=O)(OC$_2$H$_5$)$_2$ | 100<br>150<br>200 | 0/2<br>1/2<br>2/2 | No obvious symptoms posterior rigidity, anorexia symptoms persisted 4 days after closing |
| COMPOUND OF THIS INVENTION | | | |
| Cl-(phenyl) with para NH—C(=S)—NH—P(=O)(OC$_2$H$_5$)$_2$ groups | 100<br>200 | 0/1<br>0/2 | No obvious symptoms |

EXAMPLE 24

Dogs on toxicity tests are dosed via gelatin capsules in the morning approximately 2 hours after feeding. Dogs are fed moistened Purina High Protein ® Dog Meal once a day. Uneaten food is removed after 2–3 hours. Water is available ad libitum. Dogs are observed at half hour intervals during the day for signs of toxicity. Toxic symptoms observed include: emesis, anorexia, salivation, diarrhea, tremors, depression and ataxia. On succeeding days, dogs are observed at 8:15 AM, while feeding, and 2–3 times in the afternoon until toxic symptoms are no longer evident.

TABLE VII

Toxicity in dogs

| COMPOUND | SOD mg/kg | Emesis | Transient Anorexia | *Severe Toxicity |
|---|---|---|---|---|
| (phenyl) with ortho NH—C(=S)—NH—P(=O)(OC$_2$H$_5$)$_2$ and NH—C(=S)—NH—P(=O)(OC$_2$H$_5$)$_2$ | 25<br>50<br>75 | 3/5<br>1/5<br>⅜ | 0/5<br>2/5<br>⅜ | 0/5<br>1/5<br>¼ |

COMPOUNDS OF THE INVENTION

TABLE VII-continued

Toxicity in dogs

| COMPOUND | SOD mg/kg | Number of Dogs Showing Adverse Symptoms/total treated | | |
|---|---|---|---|---|
| | | Emesis | Transient Anorexia | *Severe Toxicity |
| (structure: phenyl with Cl, two NH—C(S)—NH—P(O)(OC$_2$H$_5$)$_2$ groups) | 25 | 1/3 | 1/3 | 0/3 |
| | 50 | 0/3 | 0/3 | 0/3 |
| | 75 | 2/3 | 2/3 | 0/3 |
| (structure: phenyl with OCH$_3$, two NH—C(S)—NH—P(O)(OC$_2$H$_5$)$_2$ groups) | 25 | 1/3 | 0/3 | 0/3 |
| | 50 | 1/3 | 3/3 | 0/3 |
| | 75 | 0/3 | 1/3 | 0/3 |

EXAMPLE 25

Evaluation (Efficacy) Test in Pigs

Animals

Fourteen Yorkshire X Hampshire cross pigs (barrows and gilts), approximately six weeks of age, are each experimentally infected with 1000 *Ascaris suum* eggs, and 5000 larvae of Oesophagostomum spp. by mouth. The animals are offered swine grower ration (composition hereinbelow described) and water ad libitum.

Procedure

Fifty-nine days post infection the number of eggs of *A. summ* per gram of feces is determined for each animal. This number is used as the basis for distributing the pigs into treatment groups of seven animals each.

Body weights are recorded the day before treatment to determine drug dosages. One group serves as infected nonmedicated control and the other group receives the drug orally, in a gelatine capsule at a rate of 50 mg/kg body weight. Three days post treatment the animals are sacrificed, the small intestine, cecum and large intestine of each pig is stripped and examined for adult worms. In the case of Oesophagostmum the contents of the large intestine is examined for worms.

The worm counts per group are averaged, and percent efficacy is calculated using the formula:

$$\% \text{ Efficacy} = \frac{\text{Av. No. of non-medicated} - \text{Av. No. of medicated}}{\text{Av. No. of non-medicated}} \times 100$$

The data obtained are recorded in Table VIII below.

TABLE VIII

Efficacy of a compound of the invention for the control of helminths in pigs

| Treatment | Dosage mg/kg body weight | Small Intestine *A. suum* | | Large Intestine Oesophagostomium spp. | |
|---|---|---|---|---|---|
| | | Ave. No. of worms retained | % Efficacy | Ave. No. of worms retained | % Efficacy |
| Control | 0 | 54 | — | 43 | — |
| (structure: Cl-phenyl with two NH—C(S)—NH—P(O)(OC$_2$H$_5$)$_2$ groups) | 50 | 0 | 100 | 0 | 100 |

| Swine Grower Ration | | |
|---|---|---|
| Ingredients | % | % |
| Ground yellow corn | 75 | 75 |
| Hog Chow* | 25 | |
| | 100 | |
| *Analysis of Hog Chow: | | % |
| Crude protein, not less than | | 36.0 |
| Crude fat, not less than | | 0.5 |
| Crude fiber, not more than | | 7.0 |

-continued

| Swine Grower Ration | |
|---|---|
| Calcium, not less than | 3.2 |
| Calcium, not more than | 4.2 |
| Phosphorus, not less than | 1.7 |
| Iodine, not less than | 0.0003 |
| Salt (NaCl), not less than | 2.3 |
| Salt (NaCl), not more than | 3.3 |

INGREDIENTS

Processed grain by-products, animal protein products, plant protein products, cane molasses, forage products, vitamin A supplement, D activated animal sterol, vitamin B-12 supplement, riboflavin supplement, methionine hydroxy analog, calcium, niacin, biotin, choline chloride, calcium pantothenate, defluorined phosphate, calcium carbonate, iodized salt, sodium selenite, iron carbonate, iron sulfate, manganous oxide-copper sulfate, cobalt carbonate, zinc oxide.

EXAMPLE 26

Evaluation of the Efficacy of Compounds of the invention for the control of *Strongyloides ransomi*

Animals

Thirty-five Yorkshire X Hampshire cross pigs (barrows and gilts), apprximately six wks of age, are each experimentally infected with *Strongyloides ransomi* larvae by mouth. The animals are offered swine grower ration (composition given in Example 32) and water ad libitum.

Procedure

Thirty days post infection feces samples are collected from each pig and worm egg counts made. One day later (the day before treatment) body weights are recorded and the pigs distributed into groups of seven based on worm egg counts. One group serves as infected non-medicated controls, the other groups receive the respective drug as a single oral dose (SOD) administered in a gelatin capsule at the mg/kg body weight rates indicated in Table IX below. Four days post treatment the animals are sacrificed, the stomach and small intestine of each animal are removed and worm counts are made. The counts are averaged per group and percent efficacy determined using the formula:

% Efficacy $$\frac{\text{Av. No. of non-medicated} - \text{Av. No. of medicated}}{\text{Av. No. of non-medicated}} \times 100$$

The data obtained are recorded in Table IX below.

TABLE IX

Efficacy of compounds of the invention for the control of *Strongyloides ransomi* infections in Pigs

| Treatment | Dosage mg/kg | Ave. No. of *S. ransomi* | Efficacy |
|---|---|---|---|
| Control | 0 | 273 | — |

TABLE IX-continued

Efficacy of compounds of the invention for the control of *Strongyloides ransomi* infections in Pigs

| Treatment | Dosage mg/kg | Ave. No. of *S. ransomi* | Efficacy |
|---|---|---|---|
| NH—C(=S)—NH—P(=O)(OC₂H₅)₂ substituted phenyl, para NH—C(=S)—NH—P(=O)(OC₂H₅)₂ | 50 | 176 | 35 |
| 2-Cl derivative | 25 | 205 | 25 |
|  | 50 | 10 | 96 |
| 2-CH₃O derivative | 50 | 0 | 100 |

EXAMPLE 27

Anthelmintic Activity (A) Single Active Ingredient

Testing is done in young mongrel dogs with natural or experimental infections of one or more of the following helminths: Hookworms—*Ancylostoma caninum, Uncinaria stenocephala;* Roundworms—*Toxascaris leonina;* Whipworms—*Trichuris vulpis.* Dogs are determined to be infected by finding eggs in the feces.

Compounds are administered at levels of 1–25 mg/kg as a single oral dose in a gelatin capsule. Dogs are not starved prior to treatment.

After dogs are treated, all feces are collected and washed through 80-mesh screens. Material retained on the screen is examined for worms which are identified and counted. Dogs are necropsied after their feces has been negative for worms for two days. At necropsy the worms remaining in the intestines are counted and the number remaining compared with those passed to fine percent efficacy of the compound. Data obtained are reported in Table X below.

TABLE X

Oral Efficacy in Dogs
% Efficacy (No. of Dogs) Using the Compound:

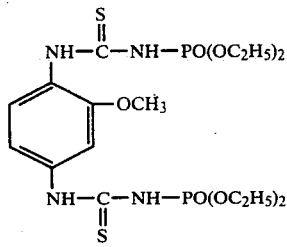

| Dose (mg/kg) | Tsp | Dc | Ac | Us | Tc | Tl | Tv |
|---|---|---|---|---|---|---|---|
| 50 | 100(2) | — | 100(3) | 100(2) | 100(5) | — | 79(5) |
| 35 | — | — | 100(1) | — | 95(4) | — | 100(1) |
| 20 | 100(1) | — | — | — | 77(3) | — | 45(1) |
| 10 | — | — | 100(1) | — | 16(1) | — | 21(1) |
| 5 | 100(1) | 100(1) | 96(10) | 100(1) | 36(4) | — | 100(1) |
| 2.5 | 94(9) | — | 74(9) | 100(5) | 32(4) | 76(6) | 7(1) |
| 1 | 100(1) | — | 32(6) | 13(1) | 0(1) | 23(5) | — |

[Structure: 2-Cl substituted phenylene bis(NH-C(=S)-NH-PO(OC₂H₅)₂)]

| Dose (mg/kg) | Tsp | Dc | Ac | Us | Tc | Tl | Tv |
|---|---|---|---|---|---|---|---|
| 50 | — | — | 100(1) | — | 63(3) | — | — |
| 10 | — | — | 93(1) | — | 0(1) | — | — |
| 5 | 92(2) | 0(1) | 100(2) | — | 17(2) | — | 100(1) |
| 2.5 | 62(12) | — | 52(11) | 65(5) | 38(6) | 98(5) | 13(7) |
| 1 | 100(2) | — | 25(6) | 71(1) | 14(1) | 17(2) | — |

[Structure: unsubstituted p-phenylene bis(NH-C(=S)-NH-PO(OC₂H₅)₂)]

| Dose (mg/kg) | Tsp | Dc | Ac | Us | Tc | Tl | Tv |
|---|---|---|---|---|---|---|---|
| 2.5 | 100(1) | — | — | — | 21(1) | — | 0(1) | where:
Tsp. = Taenia sp.
Dc = *Dipylidium caninum*
Ac = *Ancylostoma caninum*
Us = *Uncinaria Stenocephala*
Tc = *Toxocara canis*
Tl = *Toxoscaris Leonina*
Tv = *Trichuris vulpis*

We claim:

1. An anthelmintic diphosphoramidate compound of the structure:

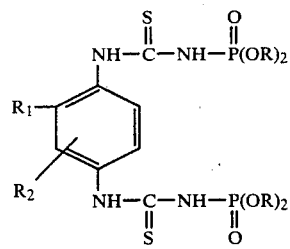

wherein R is alkyl ($C_1$–$C_4$); $R_1$ represents a member selected from the group consisting of alkyl ($C_1$–$C_4$), chloro, bromo, iodo, $R_3O$, $R_3S$ and $CF_3$; $R_2$ represents hydrogen methyl and chloro; $R_3$ represents a member selected from the group consisting of alkyl ($C_1$–$C_4$), benzyl and phenyl.

2. The compound according to claim 1, wherein R is alkyl ($C_1$–$C_4$); $R_1$ represents a member selected from the group consisting of methyl, methoxy, benzyloxy, phenoxy, methylthio, n-propylthio, benzylthio, phenylthio, chloro, bromo, iodo and $CF_3$; $R_2$ represents hydrogen, methyl or chloro.

3. The compound according to claim 1, having the structure:

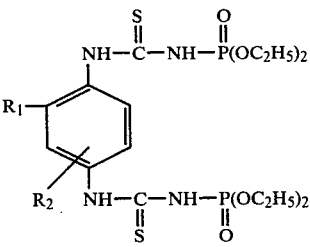

wherein $R_1$ is a member selected from the group consisting of methoxy, phenoxy, methylthio, n-propylthio, benzylthio, phenylthio, chloro, bromo, iodo and $CF_3$; $R_2$ represents hydrogen, methyl or chloro.

4. The compound according to claim 1, {(2-iodo-p-phenylene)bis[iminothiocarbonoyl)]}diphosphoramidic acid, tetraethyl ester.

5. The compound according to claim 1, {(2-chloro-p-phenylene)bis[iminothiocarbonyl)]}diphosphoramidic acid, tetraethyl ester.

6. The compound according to claim 1 {(2-chloro-p-phenylene)bis[imino(thiocarbonyl)]diphosphoramidic acid, tetraisopropyl ester.

7. The compound according to claim 1, (2-methoxy-p-phenylene)bis[imino(thiocarbonyl)]diphosphoramidic acid, tetraethyl ester.

8. The compound according to claim 1, {(2-methoxy-p-phenylene)bis[imino(thiocarbonyl)]}diphosphoramidic acid, tetraisopropyl ester.

9. The compound according to claim 1, {(2-bromo-p-phenylene)bis[imino(thiocarbonyl)]}diphosphoramidic acid, tetraethyl ester.

10. The compound according to claim 1, {[2-trifluoromethyl)-p-phenylene]bis[imino(thiocarbonyl)]}-diphosphoramidic acid, tetraethyl ester.

11. The compound according to claim 1, {(2-3-dichloro-p-phenylene)bis[imino(thiocarbonyl)]}diphosphoramidic acid, tetraethyl ester.

12. The compound according to claim 1, {[2-(methylthio)-p-phenylene]bis[imino(thiocarbonyl)]}diphosphoramidic acid, tetraethyl ester.

13. The compound according to claim 1, {[2-(n-propylthio)-p-phenylene]bis[imino(thiocarbonyl)]}diphosphoramidic acid, tetraethyl ester.

14. The compound according to claim 1, {[2-chloro-5-(n-propylthio)-p-phenylene]bis[imino(thiocarbonyl)]}diphosphoramidic acid, tetraethyl ester.

15. The compound according to claim 1, {[2-chloro-3-(n-propylthio)-p-phenylene]bis[imino(thiocarbonyl)]}diphosphoramidic acid, tetraethyl ester.

16. The compound according to claim 1, {(2-chloro-3-methoxy-p-phenylene)bis[imino(thiocarbonyl)]}diphosphoramidic acid, tetraethyl ester.

17. The compound according to claim 1, {(2-chloro-5-methoxy-p-phenylene)bis[imino(thiocarbonyl)]}diphosphoramidic acid, tetraethyl ester.

* * * * *